(12) United States Patent
Engel et al.

(10) Patent No.: US 10,300,486 B2
(45) Date of Patent: May 28, 2019

(54) DRY CHEMISTRY CONTAINER

(71) Applicant: STAT-DIAGNOSTICA & INNOVATION, S.L., Barcelona (ES)

(72) Inventors: Holger Engel, Barcelona (ES); Jordi Carrera Fabra, Barcelona (ES)

(73) Assignee: STAT-DIAGNOSTICA & INNOVATION, S.L. (ES)

( * ) Notice: Subject to any disclaimer, the term of this patent is extended or adjusted under 35 U.S.C. 154(b) by 144 days.

(21) Appl. No.: 15/210,744

(22) Filed: Jul. 14, 2016

(65) Prior Publication Data
US 2017/0014826 A1 Jan. 19, 2017

Related U.S. Application Data

(60) Provisional application No. 62/193,956, filed on Jul. 17, 2015.

(51) Int. Cl.
*B01L 3/00* (2006.01)
*F26B 5/06* (2006.01)
(Continued)

(52) U.S. Cl.
CPC ............... *B01L 3/523* (2013.01); *B01L 3/508* (2013.01); *B01L 3/502715* (2013.01); *F26B 5/06* (2013.01); *G01N 1/42* (2013.01); *B01L 2200/025* (2013.01); *B01L 2200/027* (2013.01); *B01L 2200/0621* (2013.01); *B01L 2200/0678* (2013.01); *B01L 2200/10* (2013.01); *B01L 2200/141* (2013.01); *B01L 2200/16* (2013.01);
(Continued)

(58) Field of Classification Search
CPC .... B01L 3/50825; B01L 3/5082; B01L 3/508; B01L 3/50; B01L 3/523; B01L 3/52; B65D 51/24; B65D 51/00

USPC ........ 436/180; 215/307, 200, 256, 254, 253, 215/250
See application file for complete search history.

(56) References Cited

U.S. PATENT DOCUMENTS 7,625,760 B2 * 12/2009 Kitaguchi ......... B01L 3/502715
422/562
9,062,342 B2 6/2015 Fabra et al.
(Continued)

FOREIGN PATENT DOCUMENTS

EP 2 089 159 B1 1/2013
WO WO 97/12681 * 4/1997 ............... B01L 3/14

OTHER PUBLICATIONS

International Search Report and Written Opinion directed to related International Application No. PCT/IB2016/054246, dated Oct. 5, 2016; 10 pages.

*Primary Examiner* — Christine T Mui
(74) *Attorney, Agent, or Firm* — Sterne, Kessler, Goldstein & Fox P.L.L.C.

(57) ABSTRACT

A microfluidic system is presented that includes a cartridge and a container. The cartridge includes a plurality of microfluidic channels coupled to one or more chambers. The container holds dry chemicals and includes a housing with a first opening and a second opening smaller than the first opening. The container is designed to be inserted into an opening of the cartridge, such that the container is independently secured within the opening. The insertion of the container allows for the container to be fluidically coupled with a microfluidic channel of the plurality of microfluidic channels via the second opening.

15 Claims, 10 Drawing Sheets

(51) Int. Cl.
*G01N 1/42* (2006.01)
*B65D 51/24* (2006.01)
*G01N 35/10* (2006.01)

(52) U.S. Cl.
CPC ... *B01L 2300/042* (2013.01); *B01L 2300/047* (2013.01); *B01L 2300/048* (2013.01); *B01L 2300/0627* (2013.01); *B01L 2300/0816* (2013.01); *B01L 2300/0832* (2013.01); *B01L 2300/0867* (2013.01); *G01N 2035/1055* (2013.01)

(56) References Cited

U.S. PATENT DOCUMENTS

| | | | |
|---|---|---|---|
| 2004/0126783 A1* | 7/2004 | Bortolin | B01L 3/502 435/6.12 |
| 2007/0287149 A1 | 12/2007 | Shomi et al. | |
| 2009/0061450 A1 | 3/2009 | Hunter | |
| 2015/0111215 A1 | 4/2015 | Ross et al. | |

* cited by examiner

DRY CHEMISTRY CONTAINER

CROSS REFERENCE TO RELATED APPLICATIONS

This application claims the benefit of U.S. provisional application No. 62/193,956 filed on Jul. 17, 2015, the disclosure of which is incorporated by reference herein in its entirety.

BACKGROUND

Field

Embodiments of the present invention relate to fluidic systems and methods for integrating dried chemicals with the fluidic systems.

Background

Given the complexity of molecular testing and immunoassay automation techniques, there is a lack of products that provide adequate performance to be clinically usable in near patient testing settings. Typical molecular testing includes various processes involving the correct dosage of reagents, sample introduction, lysis of cells to extract DNA or RNA, purification steps, and amplification for subsequent detection. Even though there are central laboratory robotic platforms that automate these processes, the central laboratory cannot provide the results in the needed time requirements for many tests requiring a short turnaround time.

Microfluidic devices have shown promise by acting as "labs-on-a-chip" that can provide many of the capabilities of laboratory tests in a smaller, less expensive device. However, there are many challenges with integrating various biological and chemical reagents with the microfluidic device. One example relates to the use of freeze-dried reagents (or lyophilized reagents) with microfluidic devices. Manipulation of freeze-dried reagents is complicated and complex. Freeze-dried reagents have to be kept at low humidity, which means that they have to be handled in a controlled environment. Freeze-dried reagents are powdery (sometimes referred to as "cakes"), which means they have to be handled with extreme care. Applying excessive force to freeze-dried reagents may cause them to break up, while keeping the integrity is usually important for whatever test is to be performed.

BRIEF SUMMARY

Embodiments of a container for transporting dry chemical reagents to a microfluidic device are presented. Furthermore, the integration of the container with the microfluidic device provides a near-constant controlled environment for the dry chemical reagents. Example methods of using the container and connecting the container with a microfluidic device are also presented.

In an embodiment, a microfluidic system has a cartridge and a container. The cartridge includes a plurality of microfluidic channels coupled to one or more chambers. The container is designed to hold dry chemicals and includes a housing with a first opening and a second opening smaller than the first opening. The container is designed to be inserted into an opening of the cartridge such that the container is independently secured within the opening. The insertion of the container allows for the container to be fluidically coupled with a microfluidic channel of the plurality of microfluidic channels via the second opening.

In another embodiment, a container designed to be connected with a microfluidic device includes a housing, a first lid, and a second removable lid. The housing encloses a chamber designed to hold dry chemicals and having a first opening and a second opening smaller than the first opening. The first lid is designed to cover the first opening, while the second removable lid is designed to cover the second opening. The housing is designed to be inserted into an opening of the microfluidic device, such that the container is independently secured within the opening. Upon insertion of the housing, a microfluidic channel of the microfluidic device is fluidically coupled with the chamber via the second opening.

An example method is described which includes providing a container having a housing that encloses a chamber designed to hold dry chemicals and having a first opening and a second opening smaller than the first opening, where the first opening is sealed by a first lid and the second opening is sealed with a second removable lid. The method includes removing the second removable lid from the second opening and inserting the housing into an opening of a microfluidic device, such that the container is independently secured within the opening. The method also includes flowing a liquid into the chamber, via the second opening, using a microfluidic channel of the microfluidic device.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figures 7A, 7B:
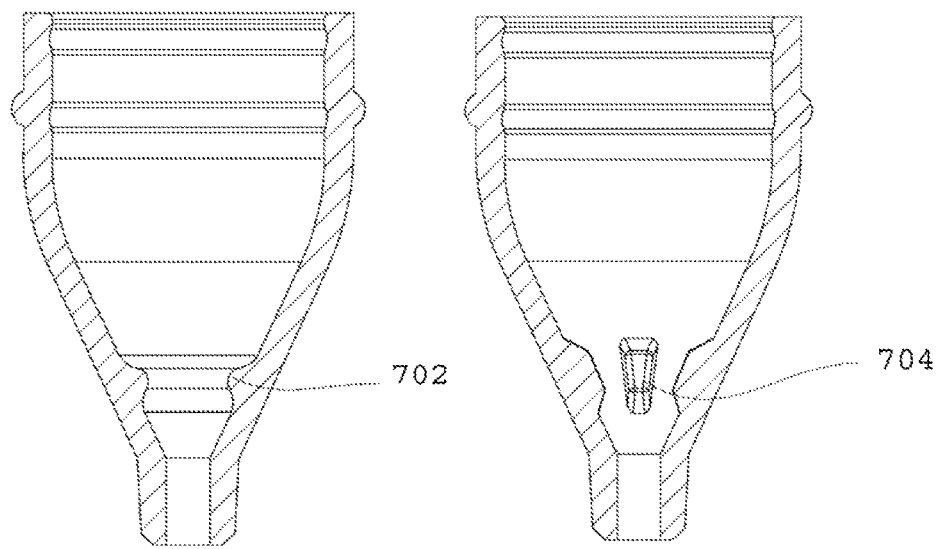

FIGS. 7A and 7B include other illustrations of the container, according to some embodiments.

Figure 8:
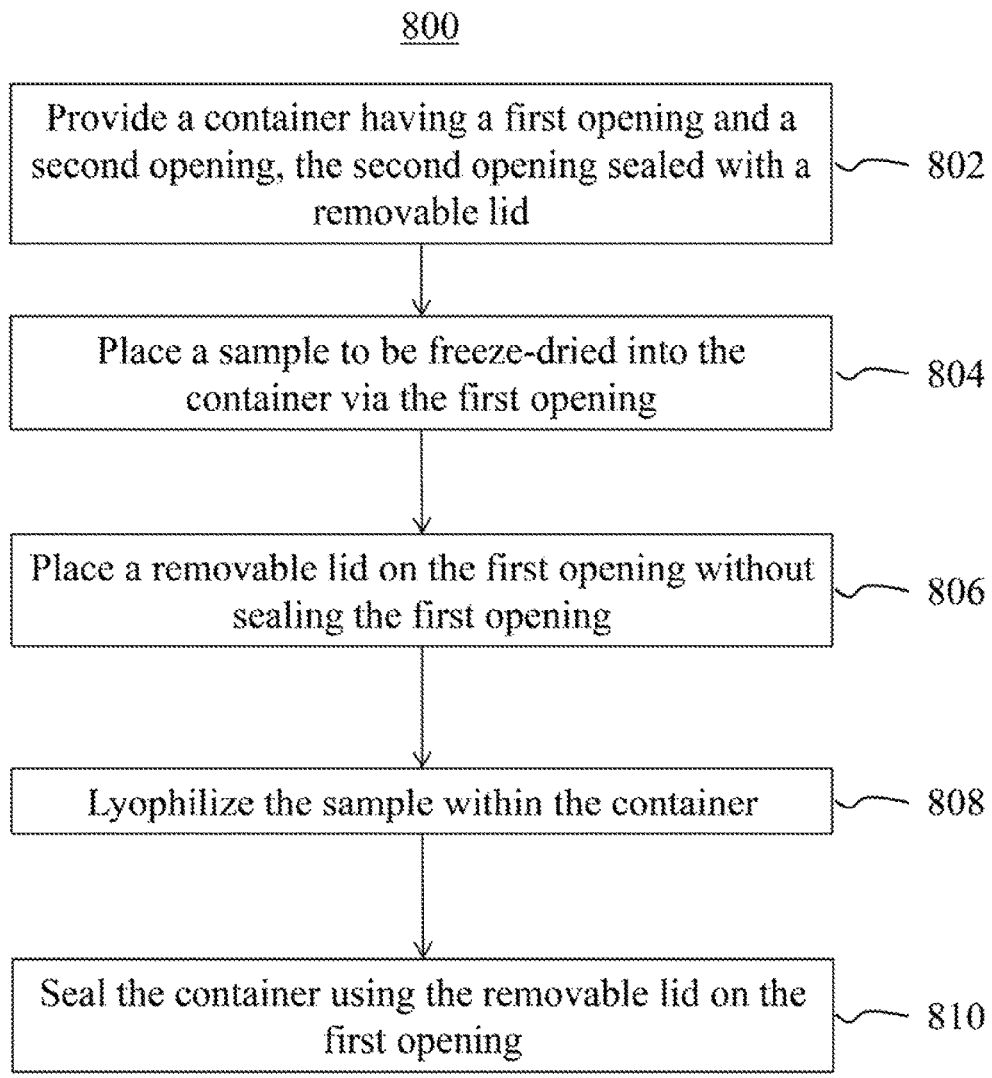
Figure 9:
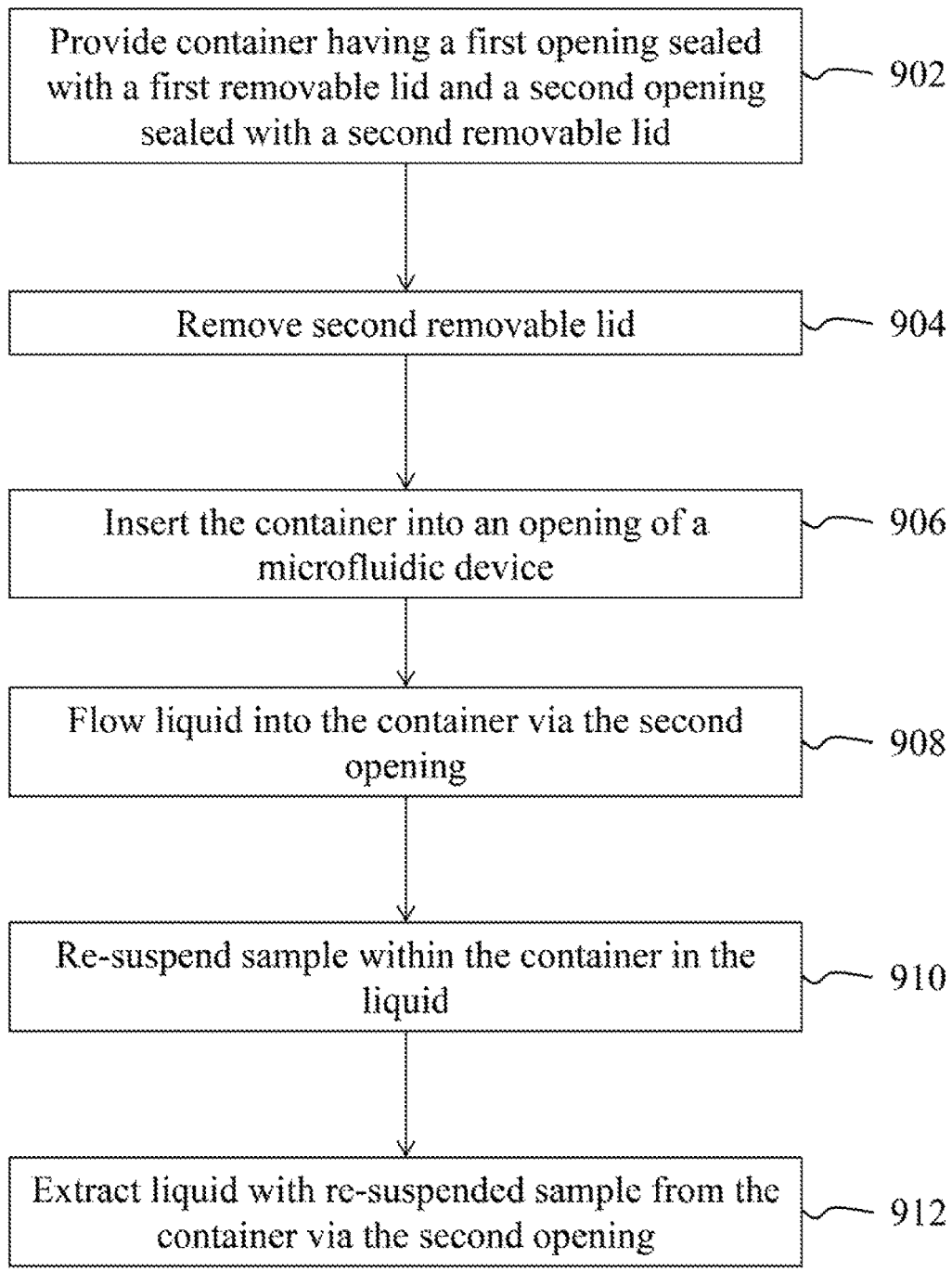

FIGS. 8 and 9 are flowcharts of example methods, according to some embodiments.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to microfluidic devices. Sample introduction to microfluidic devices can be challenging, especially when the samples include dry chemicals. An example of dry chemicals includes freeze-dried (lyophilized) chemicals. Embodiments of a container are described herein that can be used to transport the freeze-dried chemicals from the point of their lyophilization to the microfluidic device in a safe and stable manner. Although various illustrations of the container are provided herein, it should be understood that such illustrations are merely exemplary, and the specific shape and/or size of various features are not to be considered limiting on the overall concept.

Figure 1A:
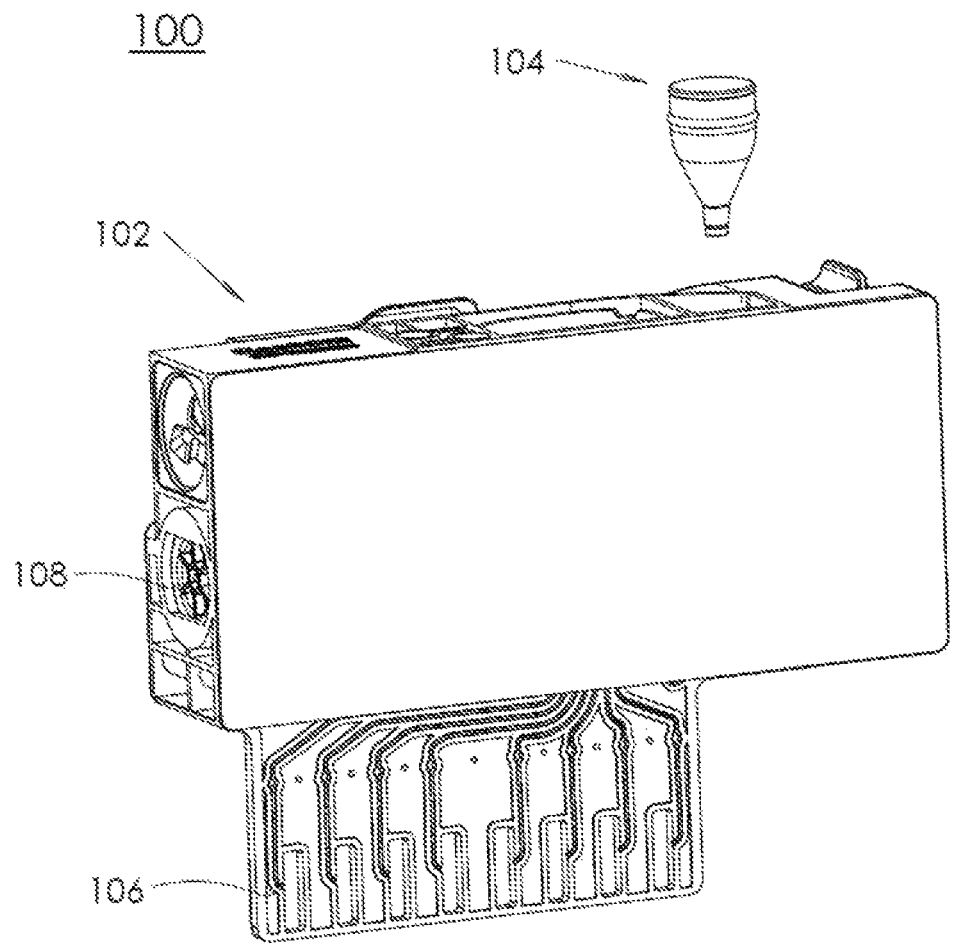
FIGS. 1A-1C illustrate various views of a microfluidic system, according to an embodiment.
Figure 1B:
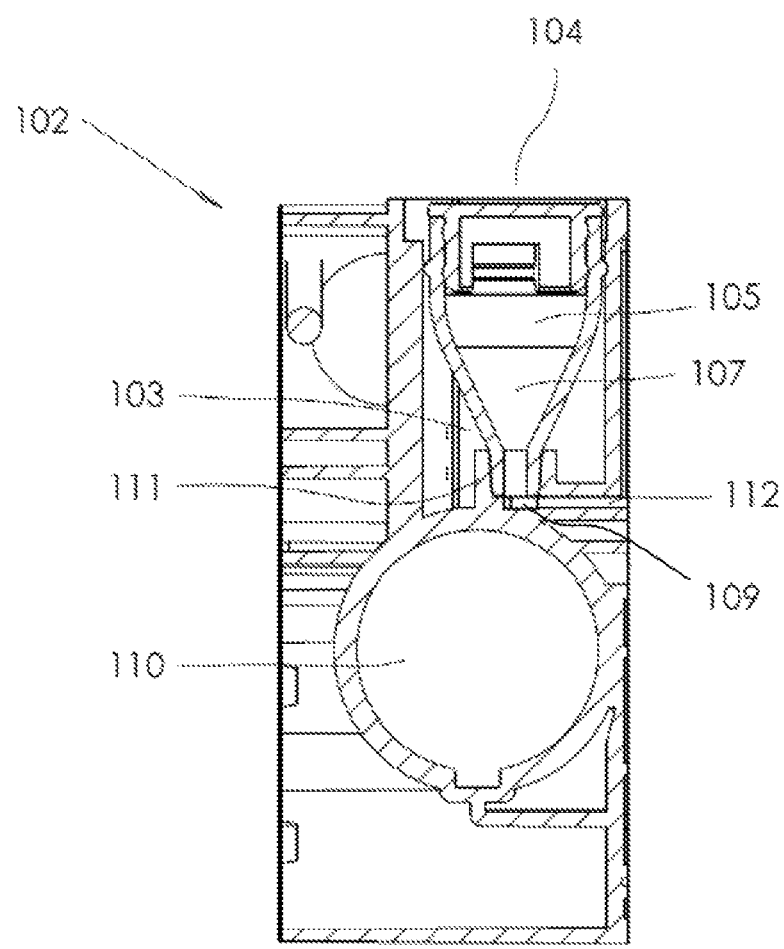
Figure 1C:
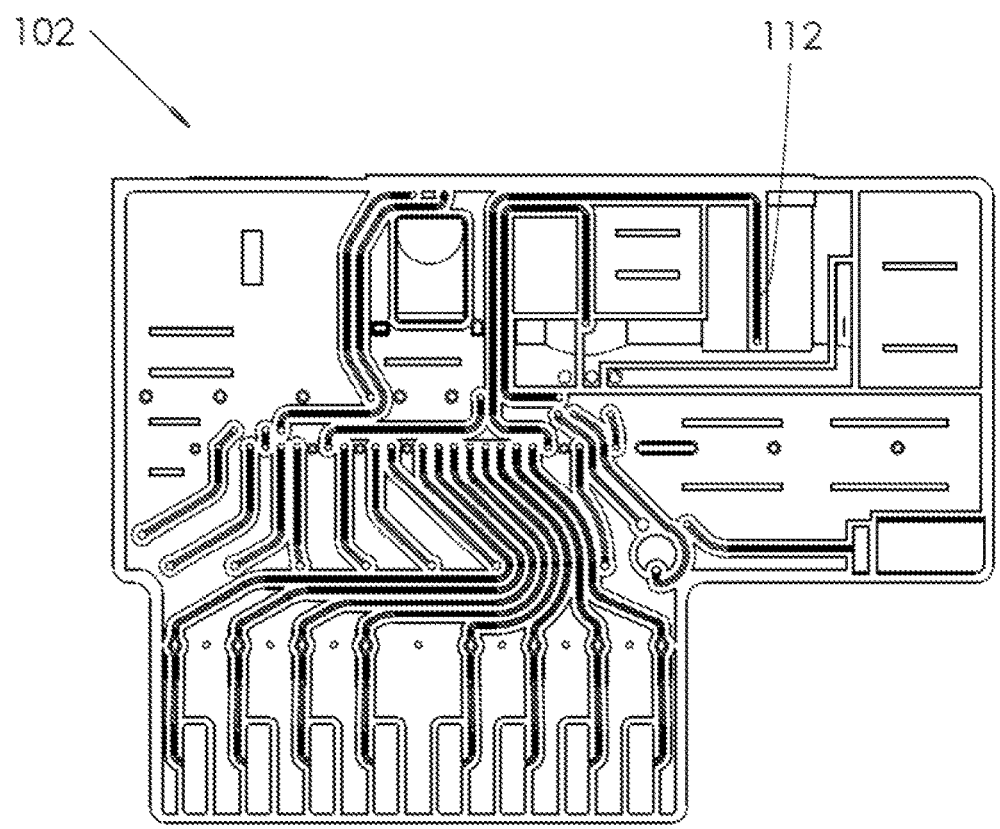

FIGS. 1A-1C illustrate various views of a microfluidic system 100, according to an embodiment. Microfluidic system 100 may generally include a microfluidic device, such as cartridge 102, and a container 104 that can fluidically interface with cartridge 102. In an example, container 104 may hold dry chemicals to be used with cartridge 102. The dry chemicals may be freeze-dried chemicals. It should be understood that container 104 may interface with any type of microfluidic device, but cartridge 102 is provided as one example of a microfluidic device.

FIG. 1A illustrates an expanded view showing container 104 before it has been connected with cartridge 102. Cartridge 102 may include a plurality of microfluidic channels and chambers. For example, cartridge 102 may include a plurality of reaction chambers 106, where reactions take place and the result of the reaction is measured via some mechanism, such as optical or electrical interrogation. Cartridge 102 may also include a transfer chamber 108 that is designed to move within cartridge 102. In one example, transfer chamber 108 moves laterally within cartridge 102. This transfer chamber may be used to align various fluid ports with the transfer chamber and control movement of the fluid throughout the various fluidic channels and chambers of cartridge 102. In one embodiment, cartridge 102 is designed to connect with container 104 via a port along a top portion of cartridge 102. In other examples, cartridge 102 connects with container 104 via a port along any side of cartridge 102. The connection between cartridge 102 and container 104 may involve pressing container 104 into cartridge 102 (e.g., to snap container 104 in place), may involve screwing or otherwise fastening container 104 into cartridge 102, or may involve connecting a fluidic channel between container 104 and cartridge 102.

FIG. 1B illustrates a cutaway portion of cartridge 102 showing how container 104 is connected, according to an embodiment. Container 104 contains a chamber 105 that holds a sample 107. In a particular embodiment, sample 107 is a freeze-dried analyte to be used for performing chemical testing with cartridge 102. A microfluidic channel 112 is used to deliver and expel fluids from chamber 105. Microfluidic channel 112 is one channel of the plurality of microfluidic channels present in cartridge 102. FIG. 1B also illustrates a central opening 110 through cartridge 102 where transfer chamber 108 can move laterally.

Placing container 104 within cartridge 102 allows container 104 to be fluidically coupled with microfluidic channel 112 of cartridge 102, according to an embodiment. It should be understood that other microfluidic channels of the plurality of microfluidic channels in cartridge 102 may be fluidically coupled with container 104 as well. Fluidically coupled generally means that the contents of container 104 may be fluidically accessed via the coupled fluidic channel. For example, fluid may enter chamber 105 via microfluidic channel 112 and re-suspend any freeze-dried reagents there. Although container 104 is shown being placed entirely within cartridge 102 in FIG. 1B, this is not required. Container 104 need only be fluidically coupled with any of the microfluidic channels of cartridge 102.

As illustrated in FIG. 1B, cartridge 102 includes an opening 103 shaped to receive the size and shape of container 104, according to an embodiment. As such, opening 103 may be capable of receiving the entire container 104. For example, opening 103 in cartridge 102 may be sized such that container 104 fits snugly within opening 103 when gentle force is applied to push container 104 down into opening 103 of cartridge 102. In another example, container 104 may be screwed into opening 103 such that microfluidic channel 112 is fluidically coupled with container 104. Container 104 may fit into opening 103 such that container 104 is independently secured within opening 103. For example, after a user or machine inserts container 104 into opening 103, container 104 remains secured within opening 103 without the need for further manipulation by the user or machine.

Microfluidic channel 112 includes a distal port 109 that may be open to the atmosphere until container 104 is fluidically coupled to microfluidic channel 112. In another embodiment, distal port 109 is covered until container 104 is placed within opening 103. For example, distal port 109 may include a removable plug that is manually removed via a human user or machine just before placement of container 104 within opening 103. In another example, distal port 109 includes a mechanically sliding, hinged, or rotatable cover that is actuated to uncover distal port 109 when container 104 is placed within opening 103.

In an embodiment, cartridge 102 may include a wall segment 111 within opening 103 that is designed to create a partition over distal port 109 of microfluidic channel 112. This partition may be sized to receive a portion of container 104 as illustrated in FIG. 1B. For example, the partition created by wall segment 111 may be sized to receive a cylindrical portion of container 104 that is smaller than a remaining cylindrical portion of container 104. Additional example geometric details regarding some embodiments of container 104 are provided herein with reference to FIGS. 2A, 2B, 3A, 3B, 4, and 5.

FIG. 1C illustrates a side view of cartridge 102, according to an embodiment. This view allows for an example visual representation of various microfluidic channels and chambers that can exist within cartridge 102. One of those microfluidic channels 112 may be used to fluidically couple with container 104.

The description herein will focus more on the design and function of container 104. Further details about an example corresponding cartridge 102 may be found in co-pending U.S. application Ser. No. 13/836,845, the disclosure of which is incorporated by reference herein in its entirety. One of skill in the art will appreciate that other microfluidic cartridges having fluid channels may instead be used with container 104.

Figures 2A, 2B:
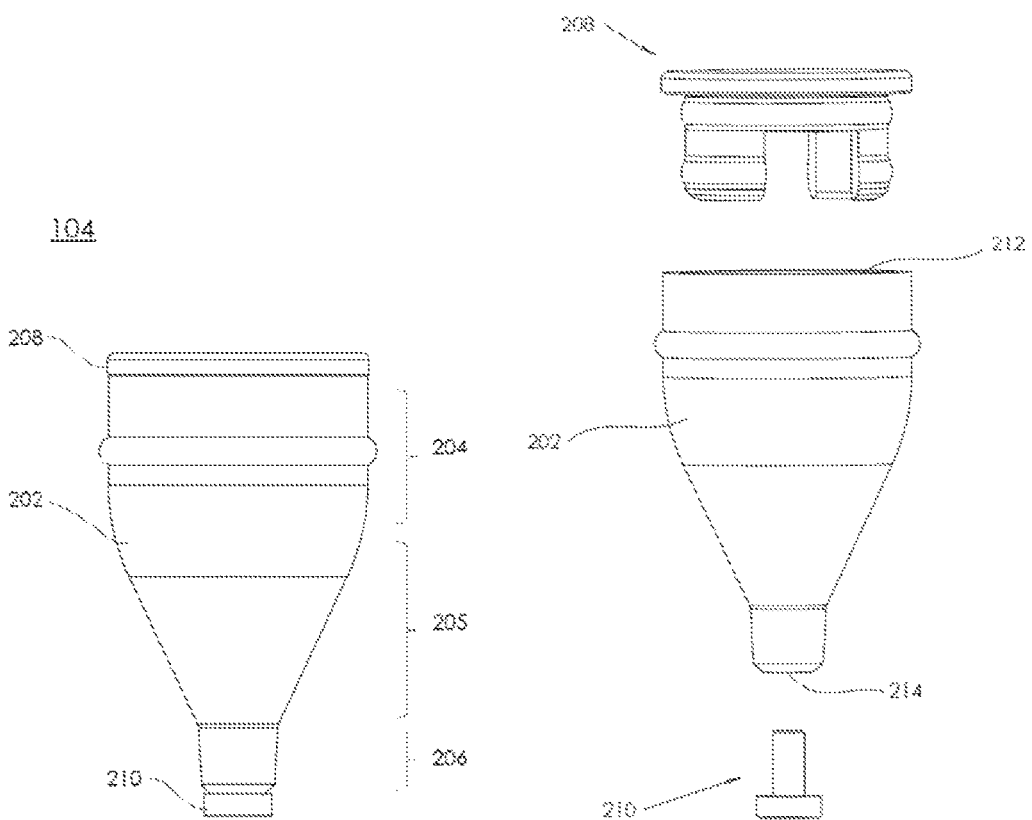
FIG. 2A is a three-dimensional illustration of a container, according to an embodiment.
FIG. 2B is another three-dimensional illustration of the container, according to an embodiment.

FIGS. 2A and 2B illustrate three dimensional renderings of container 104 and its various parts, according to some embodiments. Container 104 includes a housing 202, which encloses chamber 105 within container 104. Container 104 also includes a top lid 208 and a bottom lid 210.

Housing 202 includes a first cylindrical portion 204 and a second cylindrical portion 206. Housing 202 may be formed, for example, via injection modeling of a polymer material, such as polypropylene. The first cylindrical portion 204 has a larger diameter than the second cylindrical portion 206. For example, first cylindrical portion 204 may have a diameter between 8 and 12 millimeters while second cylindrical portion 206 may have a diameter between 3 and 5 millimeters. A total height of housing 202 may be, for example, between 13 and 20 millimeters. In one particular example, a diameter of first cylindrical portion 204 is 10 millimeters, a diameter of second cylindrical portion 206 is 5 millimeters, and a height of housing 202 is 14 millimeters. The first cylindrical portion 204 and the second cylindrical portion 206 may be connected by a sloped enclosure 205. The angle of sloped enclosure 205 may vary. In one example, the angle of sloped enclosure 205 is sufficiently steep to increase the surface area contacting the reagents kept within sloped enclosure 205. Additionally, while the figures show second cylindrical portion 206 centrally aligned with first cylindrical portion 204, one of skill in the art would understand that other alignments, such as any off-centered alignment, may instead be used.

Top lid 208 is a removable lid that may be used to seal a first opening 212 of housing 202. Bottom lid 210 is a removable lid that may be used to seal a second opening 214 of housing 202. First opening 212 is larger than second opening 214. Both top lid 208 and bottom lid 210 may be formed via, for example, injection molding of a polymer, such as polypropylene. Top lid 208 and bottom lid 210 may be suitably sized so as to seal first opening 212 and second opening 214, respectively, when the lids are inserted into their respective openings. Although first opening 212 and second opening 214 (and similarly, top lid 208 and bottom lid 210) are illustrated as being circular, this is not a requirement. The openings may be of any shape along with suitably shaped lids to seal the respective openings.

In another embodiment, top lid 208 is designed to be irremovable from first opening 212 after it has been used to seal first opening 212. For example, after placing a sample within chamber 105 of container 104, top lid 208 is used to permanently seal first opening 212, and the only way to then access the sample is via second opening 214. Container 104 may be designed to be disposable when top lid 208 is used to permanently seal first opening 212.

Figure 3A:
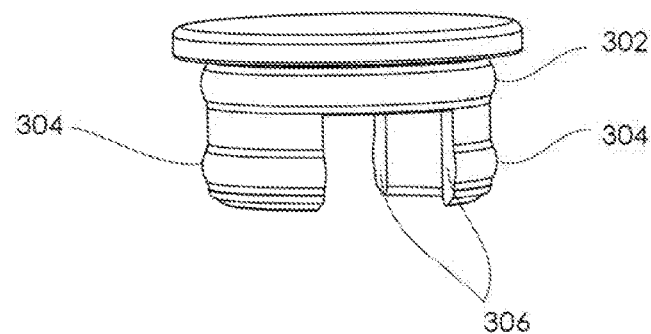
FIG. 3A is a three-dimensional illustration of a top lid to the container, according to an embodiment.

FIG. 3A illustrates an example of top lid 208. Top lid 208 includes a first protruding structure 302 which extends around a circumference of top lid 208, and second protruding structures 304 that extend around a circumference of top lid 208, except where there are slotted openings 306. First protruding structure 302 and second protruding structures 304 may be made, for example, from a rubber-like material or a pliable polymer such that the structures press against the inner wall of housing 202 to seal opening 214 from the outside environment.

Figure 3B:
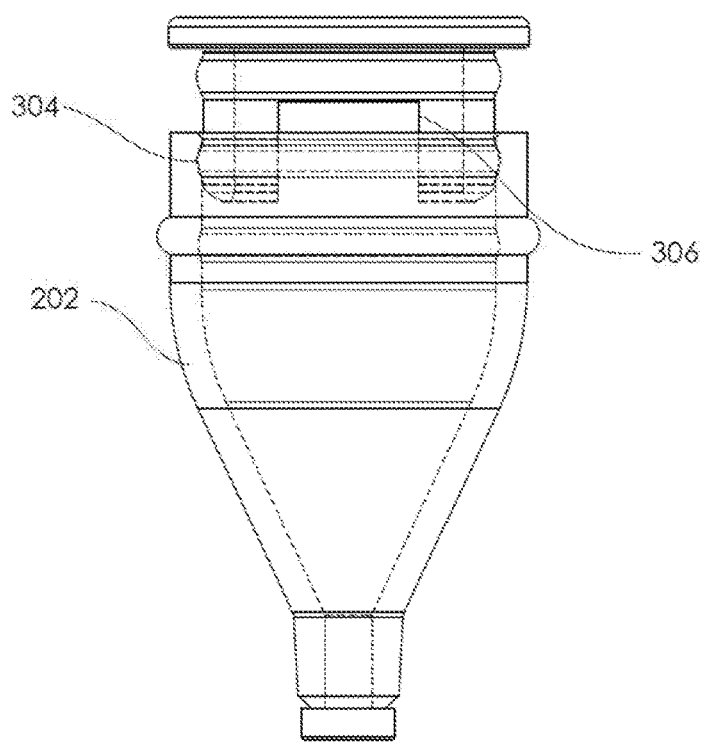
FIG. 3B is a three-dimensional illustration of the top lid with the rest of the container, according to an embodiment.

Slotted openings 306 may exist around the bottom portion of top lid 208. The size, number, and shape of slotted openings 306 are not important, as long as the openings allow air to pass through first opening 212 of housing 202 when top lid 208 is placed over first opening 212, but does not seal first opening 212. Such an arrangement is illustrated in FIG. 3B. Here, top lid 208 sits atop first opening 212 by resting the second protruding structures on a lip around first opening 212, according to an embodiment. By resting top lid 208 on the second protruding structures, slotted openings 306 still allow air to pass through first opening 212 and into container 104. This setup may be used, for example, during a freeze-drying procedure of a sample placed within chamber 105, to allow air to escape during the procedure. After the freeze-drying process is complete, top lid 208 may be pressed downward towards chamber 105 such that first protruding structure 302 seals first opening 212 and does not allow any further elements (e.g., air, moisture) to enter chamber 105.

Figure 4:
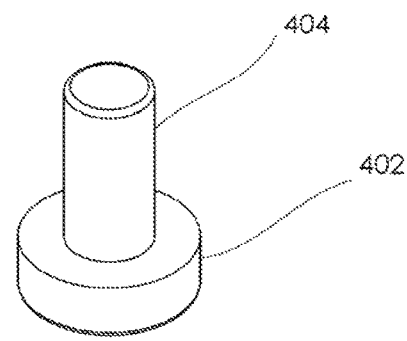
FIG. 4 is a three-dimensional illustration of a bottom lid of the container, according to an embodiment.

FIG. 4 illustrates bottom lid 210, according to an embodiment. Bottom lid 210 includes a cap 402 and a plug 404. Cap 402 may be sized to facilitate insertion and removal of bottom lid 210 into and out of second opening 214 by a user or mechanical device, while plug 404 has a diameter suitable for sealing second opening 214 when bottom lid 210 is inserted into second opening 214. Plug 404 may be made from a similar material as that used to form first protruding structure 302 and second protruding structures 304 from top lid 208. In one example, bottom lid 210 is used to seal second opening 214 up until container 104 is about to be connected with cartridge 102.

Figure 5:
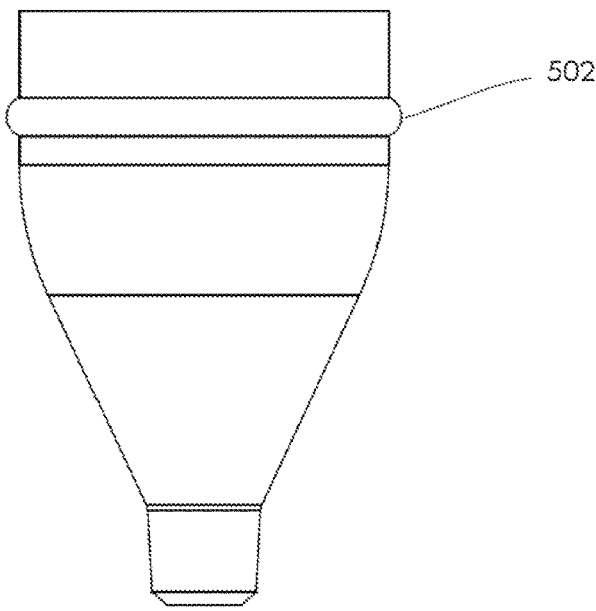
FIG. 5 is another three-dimensional illustration of the container, according to an embodiment.

FIG. 5 presents another view of container 104 with alignment structure 502, according to an embodiment. Alignment structure 502 may be provided to stabilize container 104 when it is inserted into opening 103 and fluidically coupled with microfluidic channel 112. Alignment structure 502 may function to align container 104 within opening 103 such that container 104 is fluidically coupled with microfluidic channel 112, to secure container 104 within opening 103, or to do both. For example, container 104 may be secured within opening 103 such that no fluid leakage occurs between container 104 and microfluidic channel 112. Alignment structure 502 may allow container 104 to "snap" into place when it is connected with cartridge 102. As such, the inner walls of opening 103 may include respective structures or indentations that mate with alignment structure 502. Other types of alignment structures are possible as well, such as tracks or guides that slide container 104 into place within opening 103. In another example, alignment structure 502 resembles a threaded screw that allows container 104 to be screwed into opening 103. Although only a single alignment structure 502 is illustrated, it should be understood that a plurality of alignment structures may also be used on the outside of container 104.

Figure 6:
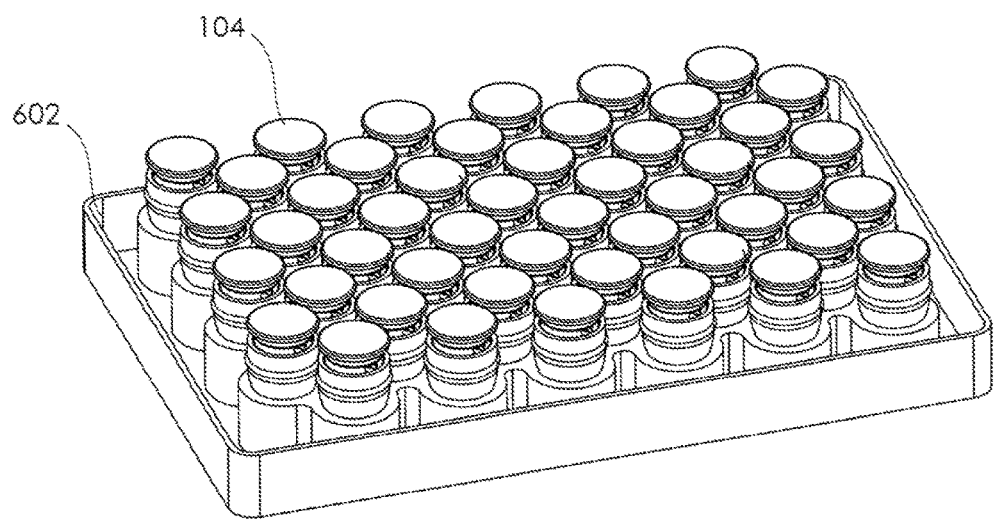
FIG. 6 is a three-dimensional illustration of a plate for holding a plurality of containers, according to an embodiment.

FIG. 6 illustrates a plurality of containers 104 placed into a plate 602. Plate 602 may be a thermally conductive material, such as aluminum, and used to hold a number of containers 104 during the sample preparation process. In one example, sample preparation includes freeze-drying reagents held within the various containers 104. Plate 602 may be placed into a lyophilizer, or any other similar device used to freeze-dry reagents, to facilitate freeze-drying of multiple samples in different containers 104.

The dried reagents within container 104 could become dislodged within the container during transportation. This may make it more difficult to suspend the reagents if they end up located far from distal port 109 where fluid is introduced into the container. In an embodiment, the inner surface of container 104 includes a grainy or any other type of texturized surface. This surface texture helps to secure the dried reagents in place while the container is being handled.

According to some other embodiments, FIGS. 7A and 7B illustrate two alternations that are made to container 104 to help secure the dried reagents in place within the container.

FIG. 7A illustrates a cross section of the container having a necking region 702, according to an embodiment. The reagents may be dried around necking region 702, such that the squeezed geometry around necking region 702 helps to secure the dried reagents in place. FIG. 7B illustrates another cross section of the container having one or more interior structures 704, according to an embodiment. Interior structures 704 may have any suitable shape and size to increase the contact surface area of the dried reagents with the interior surfaces of the container, thus helping to secure the dried reagents in place around interior structures 704. A combination of both necking region 702 and interior structures 704 may be used with the container to help secure the dried reagents.

FIG. 8 is flow chart illustrating a method 800 for preparing a sample within container 104, according to an embodiment. It should be understood that the steps shown in method 700 are not exhaustive and that other steps may be performed as well without deviating from the scope or spirit of the described embodiments.

Method 800 begins with block 802, where a container is provided that has a first opening and second opening, where the second opening is sealed with a removable lid. The first opening is larger than the second opening. At this stage, the container is empty and is ready to be used for holding a sample.

At block 804, a sample to be freeze-dried is placed within the container via the first opening. The sample may be in liquid or semi-solid form. Solid samples may be used in some circumstances, though they are unlikely to need to be freeze-dried for storage. The sample may be introduced into the container via, for example, a syringe through the first opening.

At block 806, a lid is placed on the first opening without sealing the first opening. For example, the lid may be placed on the first opening as is illustrated in FIG. 3B. Placing the lid over the opening without sealing the opening allows for air to still pass through the first opening, and will allow the air within the container to vent during the freeze-drying process.

At block 808, the sample is freeze-dried (i.e., lyophilized) within the container. The container may first be placed within a plate along with similar containers. The plate may then be placed within a lyophilizer to freeze-dry the samples within the various containers.

At block 810, the container is sealed by using the lid over the first opening to seal the first opening. In one example, the lid is pressed firmly down from its resting position over the first opening to seal the first opening. The lyophilizer may be designed to press down the lids of the various containers to seal them after the freeze-drying process is finished. The lid may also be manually pushed down to seal the container. Other sealing mechanisms known to a person of skill in the art may also be used. In an embodiment, the lid used to seal the first opening is not removable after it has been used to seal the first opening.

Once the container has been sealed after the freeze-drying process, it may be kept at ambient conditions. The container may undergo the freeze-drying process to lyophilze the sample within the container at one location, then be shipped to another location where the second lid is removed to access the sample within the container.

FIG. 9 is a flowchart illustrating a method 900 for connecting the container to a microfluidic device, according to an embodiment. It should be understood that the steps shown in method 900 are not exhaustive, and that other steps may be performed as well without deviating from the scope or spirit of the described embodiments. In some embodiments, method 900 is a continuation of method 800.

Method 900 starts at block 902 where a container is provided having a first opening sealed with a first lid, and a second opening sealed with a second removable lid. As noted above, the first lid may or may not be removable. The container provided at block 902 already contains a sample within the container. In one example, the sample within the container is a dry chemistry sample. The dry chemistry sample may be a freeze-dried sample.

At block 904, the second removable lid is removed. The second removable lid may be removed in a controlled environment, for example, within a temperature- and humidity-controlled environment. The controlled environment may have substantially no moisture in the air. The second removable lid may be removed before the container is inserted into a microfluidic device, or it may be automatically removed as part of the insertion process. In another example, the second removable lid is replaced instead with a film that stretches across the second opening. The film may be punctured to access the sample within the container. The puncturing may occur upon insertion of the container into the microfluidic device via, for example, a hollow point needle (or similar hollow point structure). In another example, the film may be punctured by a human user or machine before the container is inserted into the microfluidic device.

At block 906, the container is inserted into an opening of a microfluidic device. An example of the microfluidic device includes cartridge 102. Inserting the container into the microfluidic device may also be performed, for example, in the same controlled environment described in block 904. The opening may be sized such that it is capable of receiving the entire container within the opening. In one embodiment, the entire container is inserted into the opening of the microfluidic device. In another embodiment, the opening is sized to snugly receive at least the bottom of container 104, with a top portion of container 104 protruding from cartridge 102. The container may fit into the opening of the microfluidic device such that the container is independently secured within the opening.

The connection between the container and the microfluidic device acts to fluidically couple the container with the microfluidic device. For example, the container may be fluidically coupled with a microfluidic channel of the microfluidic device, such that fluid can be flown into and expelled from the container via the microfluidic channel. In an embodiment, the microfluidic channel is fluidically coupled with the container via the second opening.

At block 908, liquid is flown into the container via the second opening. The liquid may be an elution liquid designed to re-suspend the freeze-dried sample within the container. The liquid may be flown through a microfluidic channel of the microfluidic device to reach the container.

At block 910, the sample within the container is re-suspended in the liquid. The process may involve gentle agitation of the container, or moving the liquid into and out of the container a set number of times to facilitate the re-suspension of the sample in the liquid.

At block 912, the liquid containing the re-suspended sample is extracted via the second opening. In one example, the liquid is extracted to another chamber of the microfluidic device. The liquid may, for example, be extracted to a chamber that moves laterally within the microfluidic device.

The liquid may be extracted to specific reaction chambers of the microfluidic device, where optical or electrical sensors are used to measure various chemical and/or biological reactions.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A microfluidic system, comprising:
    a cartridge having a plurality of microfluidic channels coupled to one or more chambers;
    a container configured to hold dry chemicals and having a housing with a first opening and a second opening smaller than the first opening, wherein the container is configured to be inserted into an opening of the cartridge, such that the container is independently secured within the opening of the cartridge and is fluidically coupled with a microfluidic channel of the plurality of microfluidic channels via the second opening of the container; and
    a lid configured to cover the first opening and comprising an upper portion and a lower portion, a first protruding structure that extends around a circumference of a top portion of the lower portion of the lid, and a second protruding structure that extends around a circumference of a bottom portion of the lower portion of the lid between slotted openings through the bottom portion of the lid, wherein the slotted openings coincide with and intersect the circumference of the bottom portion, forming gaps in the second protruding structure.

2. The microfluidic system of claim 1, wherein the housing has a first cylindrical portion and a second cylindrical portion smaller than the first cylindrical portion.

3. The microfluidic system of claim 2, wherein a diameter of the first cylindrical portion is substantially equal to a diameter of the first opening and a diameter of the second cylindrical portion is substantially equal to a diameter of the second opening.

4. The microfluidic system of claim 2, wherein the container further comprises one or more structures that protrude outward from the first cylindrical portion and are configured to hold the container within the opening of the cartridge.

5. The microfluidic system of claim 4, wherein the cartridge includes respective structures or indentations that mate with the one or more structures.

6. The microfluidic system of claim 1, wherein the dry chemicals include freeze-dried reagents.

7. A container configured to connect with a microfluidic device, the container comprising:
    a housing that encloses a chamber configured to hold dry chemicals and having a first opening and a second opening smaller than the first opening;
    a first lid configured to cover the first opening and comprising an upper portion and a lower portion, a first protruding structure that extends around a circumference of a top portion of the lower portion of the first lid, and a second protruding structure that extends around a circumference of a bottom portion of the lower portion of the first lid between slotted openings through the bottom portion of the first lid, wherein the slotted openings coincide with and intersect the circumference of the bottom portion, forming gaps in the second protruding structure; and
    a second removable lid configured to cover the second opening,
    wherein the housing is configured to be inserted into an opening of the microfluidic device, such that the container is independently secured within the opening, and such that a microfluidic channel of the microfluidic device is fluidically coupled with the chamber via the second opening.

8. The container of claim 7, wherein the first lid includes a protruding structure that prevents moisture from entering into the chamber through the first opening when the first opening is covered by the first lid.

9. The container of claim 7, wherein the housing has a first cylindrical portion and a second cylindrical portion smaller than the first cylindrical portion.

10. The container of claim 9, wherein a diameter of the first cylindrical portion is substantially equal to a diameter of the first opening and a diameter of the second cylindrical portion is substantially equal to a diameter of the second opening.

11. The container of claim 9, further comprising one or more structures that protrude outward from the first cylindrical portion and are configured to hold the housing within the microfluidic device when the housing is inserted into the opening of the microfluidic device.

12. The container of claim 7, wherein the first lid includes one or more protruding structures that allows the first lid to sit overtop the first opening by resting on the one or more protruding structures without sealing the first opening.

13. The container of claim 12, wherein the slotted openings of the first lid are configured to allow air to pass through the first opening when the first lid is resting on the one or more protruding structures.

14. The container of claim 7, wherein the housing includes a necking region located closer to the second opening than the first opening, the necking region being configured to hold the dry chemicals around the necking region.

15. The container of claim 7, wherein the housing includes one or more interior structures located closer to the second opening than the first opening, the one or more interior structures being configured to hold the dry chemicals around the one or more interior structures.

* * * * *